(12) United States Patent
Pinhack

(10) Patent No.: US 9,709,336 B2
(45) Date of Patent: Jul. 18, 2017

(54) PROCESS AND APPARATUS FOR COOLING A DIGESTION VESSEL OF A CALORIMETER AFTER USE

(75) Inventor: Hubert Pinhack, Bad Krozingen (DE)

(73) Assignee: IKA-Werke GmbH & Co. KG, Staufen (DE)

( * ) Notice: Subject to any disclaimer, the term of this patent is extended or adjusted under 35 U.S.C. 154(b) by 823 days.

(21) Appl. No.: 14/110,749

(22) PCT Filed: Apr. 5, 2012

(86) PCT No.: PCT/EP2012/001513
§ 371 (c)(1),
(2), (4) Date: Oct. 25, 2013

(87) PCT Pub. No.: WO2012/139733
PCT Pub. Date: Oct. 18, 2012

(65) Prior Publication Data
US 2014/0054007 A1    Feb. 27, 2014

(30) Foreign Application Priority Data
Apr. 13, 2011 (DE) .................. 10 2011 016 956

(51) Int. Cl.
*F28C 3/00* (2006.01)
*G01K 17/00* (2006.01)
*G01N 25/20* (2006.01)
*G01N 25/48* (2006.01)
*F25D 3/10* (2006.01)

(52) U.S. Cl.
CPC ................ *F28C 3/00* (2013.01); *G01K 17/00* (2013.01); *G01N 25/20* (2013.01); *G01N 25/4826* (2013.01); *F25D 3/10* (2013.01)

(58) Field of Classification Search
CPC .. F28C 3/00; F25D 3/10; G01K 17/00; G01N 25/20; G01N 25/4826
USPC ........ 165/80.5, 104.19; 374/33, 31, E17.001
See application file for complete search history.

(56) References Cited

U.S. PATENT DOCUMENTS

| 5,547,282 A | 8/1996 | Pinhack et al. | |
|---|---|---|---|
| 2002/0013001 A1* | 1/2002 | Pinhack | G01N 25/26 436/147 |
| 2005/0265511 A1* | 12/2005 | Tobimatsu | G21C 9/004 376/283 |
| 2007/0092053 A1* | 4/2007 | Sato | G21C 9/004 376/283 |
| 2010/0255588 A1* | 10/2010 | Schenker | G01K 17/04 436/43 |

(Continued)

FOREIGN PATENT DOCUMENTS

| DE | 3042496 | 6/1982 |
|---|---|---|
| DE | 19601621 | 7/1997 |

(Continued)

*Primary Examiner* — Jianying Atkisson
*Assistant Examiner* — Raheena R Malik
(74) *Attorney, Agent, or Firm* — Gordon & Jacobson, P.C.

(57) ABSTRACT

To cool a digestion vessel (2) of a calorimeter (3) by means of a liquid coolant, a recess (4) over which the digestion vessel (2) is invented during the cooling possess and which has one or more ports (10) for a cooling liquid by means of which the inside of the digestion vessel (2) is wetted in such a way that the coolant runs down over part or the entireties of this inside of the digestion vessel (2) so as to remove the heat thereof is provided.

9 Claims, 2 Drawing Sheets

(56) References Cited

U.S. PATENT DOCUMENTS

2010/0290576 A1* 11/2010 Yamazaki ............ G21C 13/036
376/299
2010/0316087 A1* 12/2010 Pinhack ................ G01N 25/26
374/33
2014/0079090 A1* 3/2014 Pinhack ................ G01N 25/22
374/36

FOREIGN PATENT DOCUMENTS

| | | |
|---|---|---|
| GB | 2059585 | 4/1981 |
| JP | 09-178577 | 7/1997 |

* cited by examiner

PROCESS AND APPARATUS FOR COOLING A DIGESTION VESSEL OF A CALORIMETER AFTER USE

CROSS-REFERENCE TO RELATED APPLICATIONS

This application claims priority from PCT/EP2012/001513, having a filing date of Apr. 5, 2012, which claims priority from DE 10 2011 016 956.3, having a filing date of Apr. 13, 2011, which are hereby incorporated by reference herein in there entireties.

BACKGROUND OF THE INVENTION

1. Field of the Invention

The present invention relates to a method for cooling a digestion vessel for dry calorimeters, the digestion vessel being cooled after use to a temperature at which it is suitable for another use operation.

The invention also relates to an apparatus for cooling a digestion vessel for dry calorimeters, comprising a cooling means after the use, particularly for executing the above-mentioned method.

2. State of the Art

A dry combustion calorimeter with digestion vessel is known, for example, from DE 43 14 454 C1.

It is already known to cool digestion vessels of dry calorimeters after use in order to make the digestion vessel available more quickly for repeated use. It is also known to brace the digestion vessel between two brackets enclosing it whose inner sides are in thermal contact with the exterior of the digestion vessel and which, in turn, are cooled. Such a cooling method and the associated apparatus must be regarded as elaborate and also require a relatively long time for sufficient cooling.

SUMMARY OF THE INVENTION

There is therefore a need for the provision of a method and an apparatus of the type defined at the outset with which fast and effective cooling is possible.

To achieve this object, the method according to the invention is characterized in that the digestion vessel is wetted on its interior facing its reaction chamber with a coolant such that the coolant runs down over the interior of the wall of the digestion vessel.

It is therefore not attempted to cool the exterior of this digestion vessel indirectly with cooled brackets, but rather, on the contrary, in order to achieve this exterior cooling, the interior of the digestion vessel is loaded directly with a cooling liquid, which enables a substantial acceleration of the cooling process. Moreover, relatively little cooling liquid can be applied directly onto this inner side, so indirectly cooled apparatus parts are avoided.

It can be especially effective and simultaneously economical if the coolant is applied as a liquid film on the interior of the digestion vessel or the interior is sprayed with coolant such that it runs down over the interior as a film. Such a liquid film is relatively thin, which means that the application of superfluous coolant can be avoided. Nonetheless, such a film, particularly a coolant film, is commensurately effective and can enable uniform cooling.

The apparatus mentioned at the outset for achieving the abovementioned object is characterized in that it has a receptacle for accommodating the lower edge of the digestion vessel when it is in its use position, that at least one supply duct for a coolant is arranged on the interior of the receptacle which protrudes from the receptacle, and that the receptacle has an attachment device for the edge of the inner opening or of the reaction chamber of the digestion vessel so that the digestion vessel can be detachably attached on the receptacle for cooling such that it encloses the receptacle with its reaction chamber.

A relatively simple apparatus is therefore provided, namely a receptacle with coolant line arranged on the interior that is suitable and dimensioned for plugging or putting the digestion vessel on, so that the coolant fed through the supply duct, preferably water, is discharged from the receptacle and, as a result, can be applied directly to the interior of the digestion vessel. The interior of the digestion vessel can therefore be wetted directly and without cooled apparatuses with the coolant at the places that have undergone the greatest amount of heating, which is to say that the interior of the digestion vessel that was previously subjected most to heating is now also directly wetted with cooling liquid. The cooling with coolant applied directly onto the surface to be cooled must be regarded as being very effective.

It is expedient here for a plug coupling or attachment device to be provided on the lower edge area of the receptacle for the edge of the digestion vessel that is located farthest down on the digestion vessel during the cooling process and for the receptacle to have a height or lateral expansion that leaves a gap between its surface and the interior of the digestion vessel in the use position assumed during cooling or fills out the inner or reaction chamber with the exception of a gap that is left open. Such a gap between receptacle and interior of the digestion vessel enables the coolant consumption to be limited, as opposed to an arrangement in which the coolant is simply filled into the reaction chamber.

One expedient embodiment can make a provision that at least one supply duct for the coolant empties in the upper area and/or at the highest point of the receptacle. This measure makes it possible for the coolant to contact the interior of the digestion vessel in a commensurately high area thereof and to flow or run down from there to the sides and downward, thus cooling these areas as well.

In order to achieve a uniform and simultaneously economical distribution of the coolant, it is expedient here if the port of the at least one supply duct is embodied as a spray nozzle.

Better yet, the coolant can be distributed if the at least one supply duct for the coolant has in its end area at least one or more branches and, extending therefrom, several ports on the upper side of the receptacle. In this way, the distribution of the coolant within the digestion vessel that is put in place can be optimized to a large extent, and it can be achieved with greater certainty that all areas of the interior of the digestion vessel are wetted with coolant.

It is favorable for effective and time-saving cooling if the digestion vessel to be cooled has at least one temperature sensor or is or can be connected to a temperature sensor and if the temperature sensor is connected to a control unit or a regulator for the coolant supply such that, when a predetermined temperature of the digestion vessel is reached, the coolant supply can be shut off. This also makes it possible to avoid excessive cooling from being performed and time and coolant thus being wasted.

One expedient embodiment of the apparatus can make a provision that it has a connector for a temperature transfer connection to a temperature sensor of a calorimeter, so that the coolant supply for cooling the digestion vessel can be stopped when the temperature of the digestion vessel has reached a value predetermined by the calorimeter. This, too, contributes to the effectiveness of the cooling process and to the savings of coolant.

It can be expedient if the digestion vessel is dried on the interior after cooling. It can therefore be advantageous if a device for the drying of the interior of the digestion vessel surrounding it is provided at the receptacle.

It is especially favorable and advantageous if the receptacle has, in addition to the coolant line or lines, at least one gas or air supply line for supplying gas or air after the cooling process for drying. In this way, the digestion vessel can be made ready to use even more quickly than if natural drying were to be awaited.

One substantial advantage of the inventive cooling of the interior of the digestion vessel is also that a cleaning effect can also be achieved on the interior of the digestion vessel. This can optionally be supported by the drying.

In the following one exemplary embodiment of the invention is described in further detail on the basis of the partially schematic drawing.

DETAILED DESCRIPTION OF THE PREFERRED EMBODIMENTS

Figure 3:
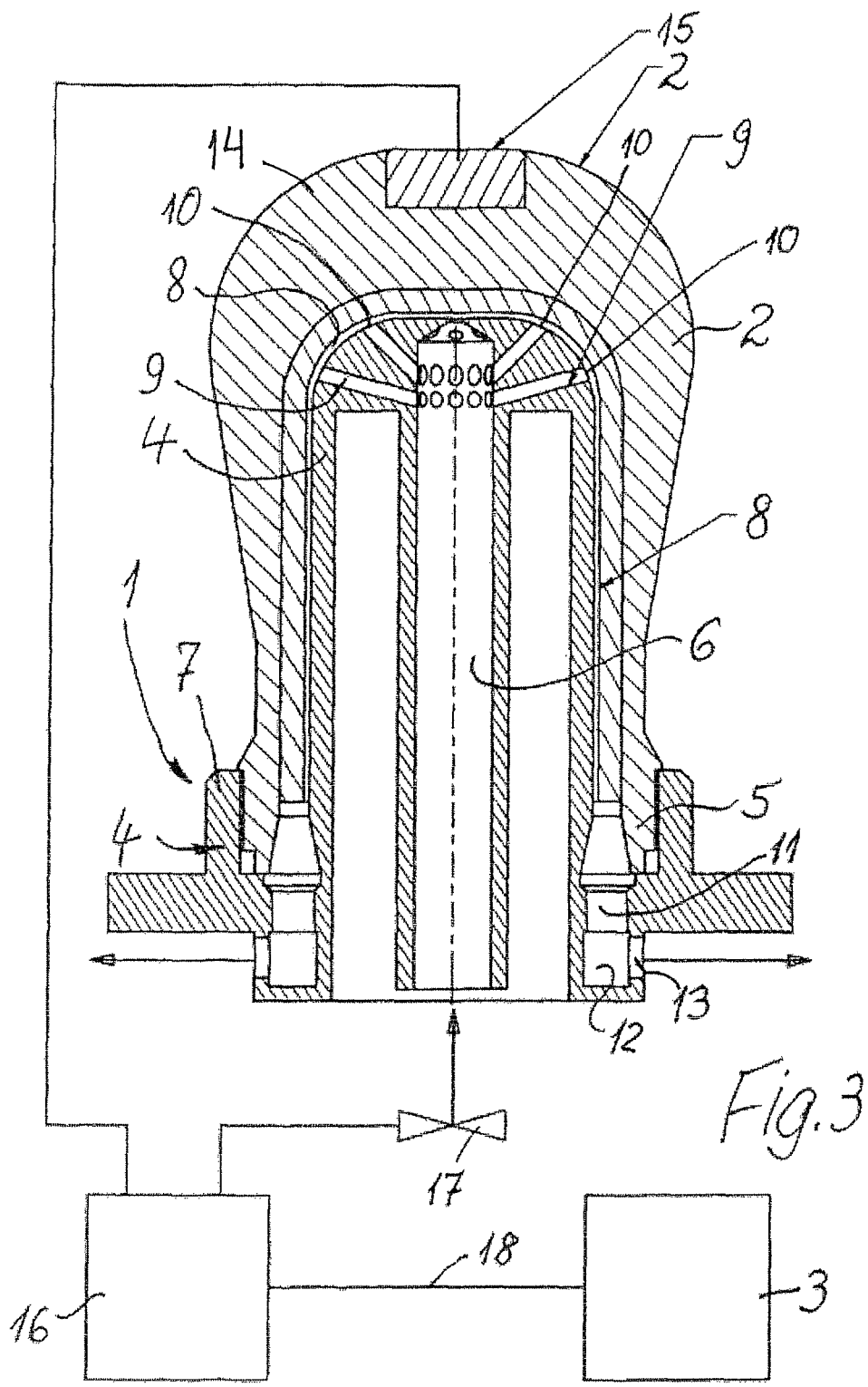
FIG. 3 shows a longitudinal section through the apparatus according to FIG. 1 with digestion vessel arranged on the receptacle, as well as a schematic view of the connection of a temperature sensor with a regulator or control device and a calorimeter.

An apparatus, referred to herein with 1, is used for the cooling of a digestion vessel 2 (FIG. 3) for a dry calorimeter 3 only indicated schematically in FIG. 3. After use, such a digestion vessel 2 is heated substantially by the combustion process carried out in it, so that it is important for quick repeated use to cool it again with commensurate speed.

Figure 1:
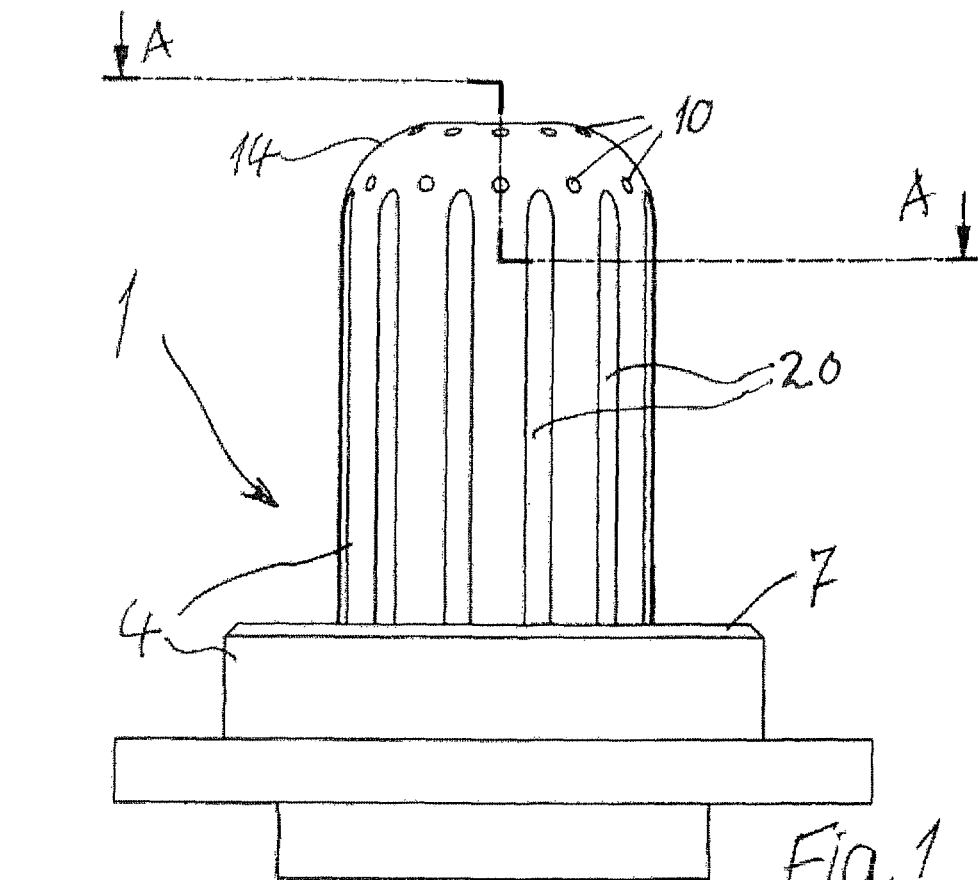
FIG. 1 shows a side view of an apparatus according to the invention for cooling a digestion vessel of a calorimeter comprising an upwardly protruding receptacle that is able to receive the lower edge of a calorimeter and on whose upper surface ports are arranged in the upper area of a supply for cooling liquid.
Figure 2:
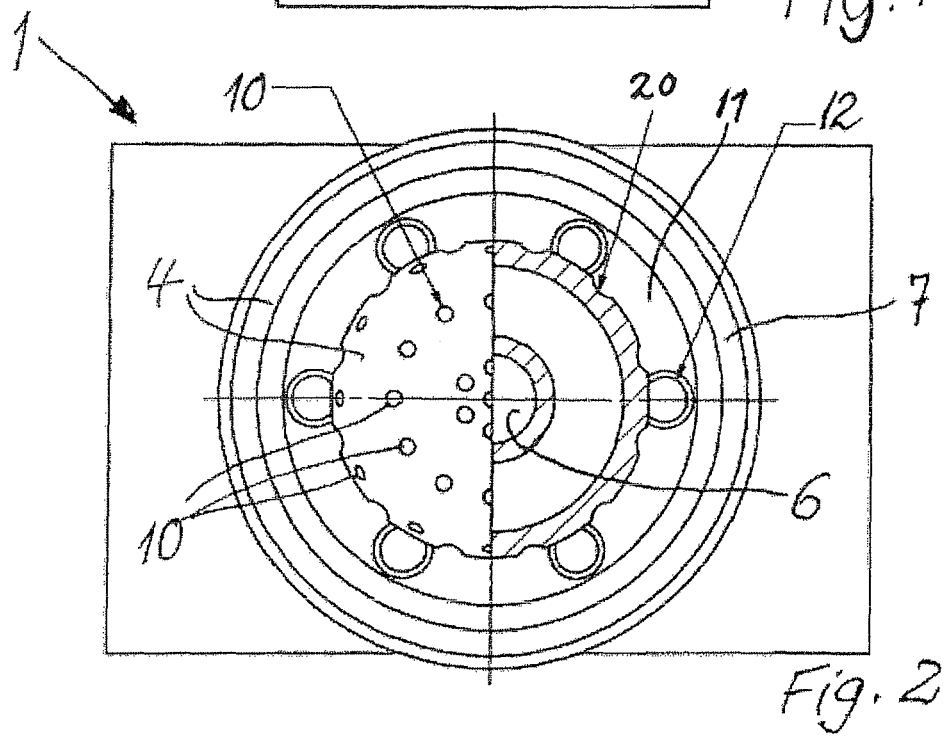
FIG. 2 shows a top view of the apparatus held partially in cross section along sectional line A-A in FIG. 1.

For this purpose, the apparatus 1 has a receptacle 4 shown in FIGS. 1 and 2 that is designed to accommodate especially the lower edge 5 of the digestion vessel 2 when in the use position according to FIG. 3 and to support and fix it during the cooling process.

In FIG. 3, one can see on the interior of this receptacle 4 a supply duct 6 for a coolant or a cooling liquid to be supplied, preferably water. This cooling liquid emerges at the surface from the receptacle 4 and, as a result, can wet and hence cool the digestion vessel 2 on its interior wall from the inside.

FIG. 3 shows that the receptacle 4 has an attachment device 7 for the edge 5 of the interior opening or the reaction chamber of the digestion vessel 2 which encloses it on the outside in the use position so that the digestion vessel 2, in order to be cooled, can be detachably attached to this receptacle 4 and its edge 7 and is mounted according to FIG. 3 in the use position.

The upright receptacle 4, which is curved or rounded in its upper area, therefore has on its lower edge area the plug coupling formed by the edge 7 for the edge 5 of the digestion vessel 2. The entire receptacle or receiving device 4 has a height and a lateral expansion that leaves a gap 8 open between its outer surface and the interior of the digestion vessel 2 or its interior chamber, as indicated in FIG. 3. In the use position, the receptacle or receiving device 4 therefore fills out the interior or reaction chamber of the digestion vessel 2 with the exception of this gap 8, which remains open.

It is also visible in FIG. 3 that the supply duct 6 for the coolant empties in the upper area 14 and/or at the highest point of the receptacle 4, so that the coolant therefore emerges in this upper area and at the highest point of the receptacle 4 when it is supplied with sufficient pressure through the supply duct 6. As a result, the interior of the digestion vessel 2 is commensurately sprayed or wetted, so that the coolant can run down over this interior or interior wall, thus bringing about effective cooling without the consumption of an unnecessarily large quantity as coolant. This quantity of coolant can be limited by the width of the gap 8.

In the sample embodiment, it can also be seen that the supply duct 6 for the coolant has in its end area several branches and, extending therefrom, several port ducts 9 with corresponding ports 10 on the surface of the receptacle 4 which can be expediently embodied as a spray nozzle. The coolant is distributed correspondingly well in this upper rounded area 14 of the receptacle 4 and transferred with commensurate uniformity to the interior of the digestion vessel 2, from where it can then run down in the gap 8 toward the edge 5, where a corresponding recess 11 is arranged in the manner of a ring in this receptacle 4 from which the coolant can be discharged via holes 12 with outlets 13.

It is also indicated in FIGS. 1 and 2 that the exterior of the receptacle 4 can have, below the area with the ports 10, discharge grooves 20 that can optionally hold and carry away excess coolant.

According to FIG. 3, the already-mentioned arch 14 of the upper end area of the receptacle 4 is adapted to the corresponding shape of the interior or reaction chamber of the digestion vessel 2 so that, in this area as well, the gap 8 has about the same width as in the other areas.

FIG. 3 also shows that the digestion vessel 2 to be cooled has at least one temperature sensor 15 that is connected to a control unit or a regulator 16 for the coolant supply such that, when a predetermined temperature of the digestion vessel 2 is reached, the coolant supply can be stopped with the aid of a valve 17. In this way, the cooling of the digestion vessel 2 for too long can be avoided. Rather, what can be achieved is that it is cooled to a favorable temperature such as is advantageous for continued use.

FIG. 3 shows, moreover, that the apparatus 1 has a connector for a temperature transmission connection 18 to a temperature sensor (not shown in further detail) of the calorimeter 3 which can also be connected to the control unit or the regulator 16, so that the coolant supply can be stopped when the temperature of the digestion vessel 2 reaches a value predetermined by the calorimeter which, in turn, can be measured again via the temperature sensor 15.

In this way, it can be achieved that the digestion vessel 2 is cooled to a temperature at which it can be used immediately in the calorimeter 3.

In a manner not shown in further detail, a device for drying the interior of the digestion vessel 2 enclosing it according to FIG. 3 can be provided on the receptacle 4, it being possible for the receptacle 4, in addition to the coolant line or lines 6 and 9, to have at least one gas or air supply line, again with port, for supplying gas or air after the cooling process, thus enabling the drying of the interior or reaction chamber of the digestion vessel 2 after wetting with cooling liquid.

With the aid of the apparatus 1, the digestion vessel 2 can therefore be loaded on its interior facing its reaction chamber with cooling liquid or water and be wetted such that this coolant or water runs at least in places or, preferably, over the surface of the interior of the wall of the reaction chamber and runs out, thus carrying the heat away. Through the arrangement of the nozzles 10 in the upper, preferably arched area 14 of the otherwise approximately cylindrical receptacle 4, the coolant is applied as a liquid film on the interior of the digestion vessel 2 and the interior is sprayed with coolant such that it runs down over this interior wall as a film, which is supported by the fact that, between this interior wall of the digestion vessel 2 and the receptacle adapted in its outer shape to this interior shape of the reaction chamber, only a gap 8 is open.

In order to cool the digestion vessel 2 of a calorimeter 3 using a liquid coolant, a receptacle 4 is provided over which the attachment device 2 is placed during the cooling process and has one or more ports 10 for a cooling liquid with which the interior of the digestion vessel 2 is wetted such that the coolant runs in places or in areas over this interior of the digestion vessel 2, thus carrying the heat thereof away.

The invention claimed is:

1. A method for cooling a digestion vessel for dry calorimeters, wherein the digestion vessel is cooled after use to a temperature at which the digestion vessel becomes suitable for another use operation, the method comprising:
    wetting the digestion vessel with a coolant on an interior surface of the digestion vessel configured for facing a reaction chamber of the digestion vessel such that the coolant runs down over the interior surface of the digestion vessel,
    wherein a plug coupling or attachment device is provided in an area at or adjacent a lower edge of a receptacle for the lower edge of the digestion vessel and that the receptacle has a height and lateral extension that leaves open a gap between an outer surface of the receptacle and the interior surface of the digestion vessel or that the receptacle fills out an interior of the reaction chamber with the exception of a gap which is left open.

2. The method as set forth in claim 1, wherein the coolant is applied as liquid film on the interior surface of the digestion vessel or the interior surface is sprayed with coolant such that it runs down over the interior surface as a film.

3. An apparatus for cooling a digestion vessel for dry calorimeters, the digestion vessel having an interior surface and defining a reaction chamber with an interior opening having a lower edge, the apparatus comprising:
    a receptacle for accommodating the lower edge of the digestion vessel in a use position, the receptacle having an interior that protrudes from the receptacle and an attachment device for the lower edge; and
    at least one supply duct for a coolant arranged on the interior of the receptacle, wherein
    in order to be cooled, the digestion vessel can be detachably attached on the receptacle such that the reaction chamber of the digestion vessel encloses the receptacle, and the digestion vessel can be wetted with a coolant supplied from the at least one supply duct to the interior surface of the digestion vessel such that the coolant runs down over the interior surface of the digestion vessel to cool the digestion vessel after use to a temperature at which the digestion vessel becomes suitable for another use operation, and
    wherein a plug coupling or attachment device is provided in an area at or adjacent the lower edge of the receptacle for the lower edge of the digestion vessel and that the receptacle has a height and lateral extension that leaves open a gap between an outer surface of the receptacle and the interior surface of the digestion vessel or that the receptacle fills out an interior of the reaction chamber with the exception of a gap which is left open.

4. The apparatus as set forth in claim 3, wherein the at least one supply duct for the coolant empties into an upper area of the receptacle and/or at a highest point of the receptacle.

5. The apparatus as set forth in claim 3, wherein a port of the at least one supply duct is embodied as a spray nozzle.

6. The apparatus as set forth in claim 3, wherein the at least one supply duct for the coolant has at an end area of the supply duct at least one or more branches and, extending therefrom, several ports on an upper side of the receptacle.

7. The apparatus as set forth in claim 3, wherein the digestion vessel to be cooled is one of provided with at least one temperature sensor or connected to a temperature sensor with a control unit or a regulator for the coolant from a coolant supply such that, when a predetermined temperature of the digestion vessel is reached, supply of the coolant from the coolant supply can be stopped.

8. The apparatus as set forth in claim 3, wherein the apparatus has a connector for a temperature transmission device to a temperature sensor of a calorimeter so that the coolant for cooling the digestion vessel can be stopped when the temperature of the digestion vessel has reached a value predetermined by the calorimeter.

9. The apparatus as set forth in claim 3, wherein the receptacle, in addition to the at least one coolant supply duct, has at least one gas or air line for supplying gas or air for drying after the cooling process.

* * * * *